United States Patent [19]

Ballance et al.

[11] Patent Number: 5,380,712

[45] Date of Patent: Jan. 10, 1995

[54] TRUNCATED HUMAN SERUM ALBUMIN POLYPEPTIDES AS PLASMA EXPANDING AGENTS

[75] Inventors: David J. Ballance, Attenborough; Edward Hinchliffe, Tutbury; Michael J. Geisow, Bingham; Peter J. Senior, Wilson, all of England

[73] Assignee: Delta Biotechnology Limited, Nottingham, England

[21] Appl. No.: 944,706

[22] Filed: Feb. 14, 1992

Related U.S. Application Data

[60] Continuation of Ser. No. 687,211, Apr. 18, 1991, abandoned, which is a division of Ser. No. 263,211, Oct. 27, 1988, abandoned.

[30] Foreign Application Priority Data

Oct. 30, 1987 [GB] United Kingdom ................. 8725529

[51] Int. Cl.$^6$ ............................................. A61K 37/02
[52] U.S. Cl. ........................................... 514/12; 514/2; 530/350; 530/363; 530/364; 435/69.6
[58] Field of Search ................. 514/2, 8, 12; 435/69.1

[56] References Cited

FOREIGN PATENT DOCUMENTS

| | | |
|---|---|---|
| 73646 | 3/1983 | European Pat. Off. . |
| 91527 | 10/1983 | European Pat. Off. . |
| 138437 | 4/1985 | European Pat. Off. . |
| 201239 | 11/1986 | European Pat. Off. . |
| 0206733 | 12/1986 | European Pat. Off. . |

OTHER PUBLICATIONS

Lawn, et al., Nucl. Acids Res. 9, 6102–6114 (1981).
Brown & Schockley, in "Lipid–Protein Interactions", 1, Ed. P. C. Jost (1982).
Galliano, et al., J. Biol. Chem. 261(9), 4283–4287 (1986).
Takahashi, et al., P.N.A.S., 84, 4413–4417 (1987).
Doyen, et al., J. Biol. Chem 257(6), 2770–2774 (1982).
Geisow & Beaven, Biochem. J. 163, 477–484 (1977).

*Primary Examiner*—Garnette D. Draper
*Assistant Examiner*—David L. Fitzgerald
*Attorney, Agent, or Firm*—R. Hain Swope; Larry R. Cassett

[57] ABSTRACT

Polypeptides corresponding to mature human serum albumin residues 1 to n, where n is between 369 and 419 inclusive, are useful as substitutes for albumin in the treatment of burns and shock in humans, the clearance of undesirable compounds, (such as bilirubin) from human blood, in laboratory growth media and in HSA assays. The polypeptides may be produced by recombinant DNA techniques, especially in yeast.

3 Claims, 9 Drawing Sheets

```
                                    10                                      20
 Asp Ala His Lys Ser Glu Val Ala His Arg Phe Lys Asp Leu Gly Glu Glu Asn Phe Lys 30                                      40
 Ala Leu Val Leu Ile Ala Phe Ala Gln Tyr Leu Gln Gln Cys Pro Phe Glu Asp His Val 50                                      60
 Lys Leu Val Asn Glu Val Thr Glu Phe Ala Lys Thr Cys Val Ala Asp Glu Ser Ala Glu 70                                      80
 Asn Cys Asp Lys Ser Leu His Thr Leu Phe Gly Asp Lys Leu Cys Thr Val Ala Thr Leu 90                                     100
 Arg Glu Thr Tyr Gly Glu Met Ala Asp Cys Cys Ala Lys Gln Glu Pro Glu Arg Asn Glu 110                                     120
 Cys Phe Leu Gln His Lys Asp Asp Asn Pro Asn Leu Pro Arg Leu Val Arg Pro Glu Val 130                                     140
 Asp Val Met Cys Thr Ala Phe His Asp Asn Glu Glu Thr Phe Leu Lys Lys Tyr Leu Tyr 150                                     160
 Glu Ile Ala Arg Arg His Pro Tyr Phe Tyr Ala Pro Glu Leu Leu Phe Phe Ala Lys Arg 170                                     180
 Tyr Lys Ala Ala Phe Thr Glu Cys Cys Gln Ala Ala Asp Lys Ala Ala Cys Leu Leu Pro 190                                     200
 Lys Leu Asp Glu Leu Arg Asp Glu Gly Lys Ala Ser Ser Ala Lys Gln Arg Leu Lys Cys 210                                     220
 Ala Ser Leu Gln Lys Phe Gly Glu Arg Ala Phe Lys Ala Trp Ala Val Ala Arg Leu Ser 230                                     240
 Gln Arg Phe Pro Lys Ala Glu Phe Ala Glu Val Ser Lys Leu Val Thr Asp Leu Thr Lys 250                                     260
 Val His Thr Glu Cys Cys His Gly Asp Leu Leu Glu Cys Ala Asp Asp Arg Ala Asp Leu 270                                     280
 Ala Lys Tyr Ile Cys Glu Asn Gln Asp Ser Ile Ser Ser Lys Leu Lys Glu Cys Cys Glu 290                                     300
 Lys Pro Leu Leu Glu Lys Ser His Cys Ile Ala Glu Val Glu Asn Asp Glu Met Pro Ala 310                                     320
 Asp Leu Pro Ser Leu Ala Ala Asp Phe Val Glu Ser Lys Asp Val Cys Lys Asn Tyr Ala 330                                     340
 Glu Ala Lys Asp Val Phe Leu Gly Met Phe Leu Tyr Glu Tyr Ala Arg Arg His Pro Asp 350                                     360
 Tyr Ser Val Val Leu Leu Leu Arg Leu Ala Lys Thr Tyr Glu Thr Thr Leu Glu Lys Cys
```

FIG. IA

|     |     |     |     |     |     |     | 370 |     |     |     |     |     |     |     | 380 |
|-----|-----|-----|-----|-----|-----|-----|-----|-----|-----|-----|-----|-----|-----|-----|-----|
| Cys | Ala | Ala | Ala | Asp | Pro | His | Glu | Cys | Tyr | Ala | Lys | Val | Phe | Asp | Glu | Phe | Lys | Pro | Leu |

|     |     |     |     |     |     |     | 390 |     |     |     |     |     |     |     | 400 |
| Val | Glu | Glu | Pro | Gln | Asn | Leu | Ile | Lys | Gln | Asn | Cys | Glu | Leu | Phe | Glu | Gln | Leu | Gly | Glu |

|     |     |     |     |     |     |     | 410 |     |     |     |     |     |     |     | 420 |
| Tyr | Lys | Phe | Gln | Asn | Ala | Leu | Leu | Val | Arg | Tyr | Thr | Lys | Lys | Val | Pro | Gln | Val | Ser | Thr |

|     |     |     |     |     |     |     | 430 |     |     |     |     |     |     |     | 440 |
| Pro | Thr | Leu | Val | Glu | Val | Ser | Arg | Asn | Leu | Gly | Lys | Val | Gly | Ser | Lys | Cys | Cys | Lys | His |

|     |     |     |     |     |     |     | 450 |     |     |     |     |     |     |     | 460 |
| Pro | Glu | Ala | Lys | Arg | Met | Pro | Cys | Ala | Glu | Asp | Tyr | Leu | Ser | Val | Val | Leu | Asn | Gln | Leu |

|     |     |     |     |     |     |     | 470 |     |     |     |     |     |     |     | 480 |
| Cys | Val | Leu | His | Glu | Lys | Thr | Pro | Val | Ser | Asp | Arg | Val | Thr | Lys | Cys | Cys | Thr | Glu | Ser |

|     |     |     |     |     |     |     | 490 |     |     |     |     |     |     |     | 500 |
| Leu | Val | Asn | Arg | Arg | Pro | Cys | Phe | Ser | Ala | Leu | Glu | Val | Asp | Glu | Thr | Tyr | Val | Pro | Lys |

|     |     |     |     |     |     |     | 510 |     |     |     |     |     |     |     | 520 |
| Glu | Phe | Asn | Ala | Glu | Thr | Phe | Thr | Phe | His | Ala | Asp | Ile | Cys | Thr | Leu | Ser | Glu | Lys | Glu |

|     |     |     |     |     |     |     | 530 |     |     |     |     |     |     |     | 540 |
| Arg | Gln | Ile | Lys | Lys | Gln | Thr | Ala | Leu | Val | Glu | Leu | Val | Lys | His | Lys | Pro | Lys | Ala | Thr |

|     |     |     |     |     |     |     | 550 |     |     |     |     |     |     |     | 560 |
| Lys | Glu | Gln | Leu | Lys | Ala | Val | Met | Asp | Asp | Phe | Ala | Ala | Phe | Val | Glu | Lys | Cys | Cys | Lys |

|     |     |     |     |     |     |     | 570 |     |     |     |     |     |     |     | 580 |
| Ala | Asp | Asp | Lys | Glu | Thr | Cys | Phe | Ala | Glu | Glu | Gly | Lys | Lys | Leu | Val | Ala | Ala | Ser | Gln |

Ala Ala Leu Gly Leu

FIG. IB

```
         10        20        30        40        50        60        70        80
GATGCACACAAGAGTGAGGTTGCTCATCGGTTTAAAGATTTGGGAGAAGAAAATTTCAAAGCCTTGGTGTTGATTGCCTT
 D  A  H  K  S  E  V  A  H  R  F  K  D  L  G  E  E  N  F  K  A  L  V  L  I  A  F 90       100       110       120       130       140       150       160
TGCTCAGTATCTTCAGCAGTGTCCATTTGAAGATCATGTAAAATTAGTGAATGAAGTAACTGAATTTGCAAAAACATGTG
 A  Q  Y  L  Q  Q  C  P  F  E  D  H  V  K  L  V  N  E  V  T  E  F  A  K  T  C 170       180       190       200       210       220       230       240
TTGCTGATGAGTCAGCTGAAAATTGTGACAAATCACTTCATACCCTTTTTGGAGACAAATTATGCACAGTTGCAACTCTT
 V  A  D  E  S  A  E  N  C  D  K  S  L  H  T  L  F  G  D  K  L  C  T  V  A  T  L 250       260       270       280       290       300       310       320
CGTGAAACCTATGGTGAAATGGCTGACTGCTGTGCAAAACAAGAACCTGAGAGAAATGAATGCTTCTTGCAACACAAAGA
 R  E  T  Y  G  E  M  A  D  C  C  A  K  Q  E  P  E  R  N  E  C  F  L  Q  H  K  D 330       340       350       360       370       380       390       400
TGACAACCCAAACCTCCCCCGATTGGTGAGACCAGAGGTTGATGTGATGTGCACTGCTTTTCATGACAATGAAGAGACAT
 D  N  P  N  L  P  R  L  V  R  P  E  V  D  V  M  C  T  A  F  H  D  N  E  E  T 410       420       430       440       450       460       470       480
TTTTGAAAAAATACTTATATGAAATTGCCAGAAGACATCCTTACTTTTATGCCCCGGAACTCCTTTTCTTTGCTAAAAGG
 F  L  K  K  Y  L  Y  E  I  A  R  R  H  P  Y  F  Y  A  P  E  L  L  F  F  A  K  R 490       500       510       520       530       540       550       560
TATAAAGCTGCTTTTACAGAATGTTGCCAAGCTGCTGATAAAGCTGCCTGCCTGTTGCCAAAGCTCGATGAACTTCGGGA
 Y  K  A  A  F  T  E  C  C  Q  A  A  D  K  A  A  C  L  L  P  K  L  D  E  L  R  D 570       580       590       600       610       620       630       640
TGAAGGGAAGGCTTCGTCTGCCAAACAGAGACTCAAATGTGCCAGTCTCCAAAAATTTGGAGAAAGAGCTTTCAAAGCAT
 E  G  K  A  S  S  A  K  Q  R  L  K  C  A  S  L  Q  K  F  G  E  R  A  F  K  A 650       660       670       680       690       700       710       720
GGGCAGTGGCTCGCCTGAGCCAGAGATTTCCCAAAGCTGAGTTTGCAGAAGTTTCCAAGTTAGTGACAGATCTTACCAAA
 W  A  V  A  R  L  S  Q  R  F  P  K  A  E  F  A  E  V  S  K  L  V  T  D  L  T  K 730       740       750       760       770       780       790       800
GTCCACACGGAATGCTGCCATGGAGATCTGCTTGAATGTGCTGATGACAGGGCGGACCTTGCCAAGTATATCTGTGAAAA
 V     T  E  C  C  H  G  D  L  L  E  C  A  D  D  R  A  D  L  A  K  Y  I  C  E  N 810       820       830       840       850       860       870       880
TCAGGATTCGATCTCCAGTAAACTGAAGGAATGCTGTGAAAAACCTCTGTTGGAAAAATCCCACTGCATTGCCGAAGTGG
 Q  D  S  I  S  S  K  L  K  E  C  C  E  K  P  L  L  E  K  S  H  C  I  A  E  V 890       900       910       920       930       940       950       960
AAAATGATGAGATGCCTGCTGACTTGCCTTCATTAGCTGCTGATTTTGTTGAAAGTAAGGATGTTTGCAAAAACTATGCT
 E  N  D  E  M  P  A  D  L  P  S  L  A  A  D  F  V  E  S  K  D  V  C  K  N  Y  A 970       980       990      1000      1010      1020      1030      1040
GAGGCAAAGGATGTCTTCCTGGGCATGTTTTTGTATGAATATGCAAGAAGGCATCCTGATTACTCTGTCGTGCTGCTGCT
 E  A  K  D  V  F  L  G  M  F  L  Y  E  Y  A  R  R  H  P  D  Y  S  V  V  L  L  L
```

FIG.2A

```
       1050      1060      1070      1080      1090      1100      1110      1120
GAGACTTGCCAAGACATATGAAACCACTCTAGAGAAGTGCTGTGCCGCTGCAGATCCTCATGAATGCTATGCCAAAGTGT
  R  L  A  K  T  Y  E  T  T  L  E  K  C  C  A  A  A  D  P  H  E  C  Y  A  K  V 1130      1140      1150      1160      1170      1180      1190      1200
TCGATGAATTTAAACCTCTTGTGGAAGAGCCTCAGAATTTAATCAAACAAAACTGTGAGCTTTTTGAGCAGCTTGGAGAG
  F  D  E  F  K  P  L  V  E  E  P  Q  N  L  I  K  Q  N  C  E  L  F  E  Q  L  G  E 1210      1220      1230      1240      1250      1260      1270      1280
TACAAATTCCAGAATGCGCTATTAGTTCGTTACACCAAGAAAGTACCCCAAGTGTCAACTCCAACTCTTGTAGAGGTCTC
  Y  K  F  Q  N  A  L  L  V  R  Y  T  K  K  V  P  Q  V  S  T  P  T  L  V  E  V  S 1290      1300      1310      1320      1330      1340      1350      1360
AAGAAACCTAGGAAAAGTGGGCAGCAAATGTTGTAAACATCCTGAAGCAAAAAGAATGCCCTGTGCAGAAGACTATCTAT
  R  N  L  G  K  V  G  S  K  C  C  K  H  P  E  A  K  R  M  P  C  A  E  D  Y  L 1370      1380      1390      1400      1410      1420      1430      1440
CCGTGGTCCTGAACCAGTTATGTGTGTTGCATGAGAAAACGCCAGTAAGTGACAGAGTCACAAAATGCTGCACAGAGTCC
  S  V  V  L  N  Q  L  C  V  L  H  E  K  T  P  V  S  D  R  V  T  K  C  C  T  E  S 1450      1460      1470      1480      1490      1500      1510      1520
TTGGTGAACAGGCGACCATGCTTTTCAGCTCTGGAAGTCGATGAAACATACGTTCCCAAAGAGTTTAATGCTGAAACATT
  L  V  N  R  R  P  C  F  S  A  L  E  V  D  E  T  Y  V  P  K  E  F  N  A  E  T  F 1530      1540      1550      1560      1570      1580      1590      1600
CACCTTCCATGCAGATATATGCACACTTTCTGAGAAGGAGAGACAAATCAAGAAACAAACTGCACTTGTTGAGCTTGTGA
  T  F  H  A  D  I  C  T  L  S  E  K  E  R  Q  I  K  K  Q  T  A  L  V  E  L  V 1610      1620      1630      1640      1650      1660      1670      1680
AACACAAGCCCAAGGCAACAAAAGAGCAACTGAAAGCTGTTATGGATGATTTCGCAGCTTTTGTAGAGAAGTGCTGCAAG
  K  H  K  P  K  A  T  K  E  Q  L  K  A  V  M  D  D  F  A  A  F  V  E  K  C  C  K 1690      1700      1710      1720      1730      1740      1750      1760
GCTGACGATAAGGAGACCTGCTTTGCCGAGGAGGGTAAAAAACTTGTTGCTGCAAGTCAAGCTGCCTTAGGCTTATAACA
  A  D  D  K  E  T  C  F  A  E  E  G  K  K  L  V  A  A  S  Q  A  A  L  G  L 1770      1780
TCTACATTTAAAAGCATCTCAG
```

FIG. 2B

TRUNCATED HUMAN SERUM ALBUMIN POLYPEPTIDES AS PLASMA EXPANDING AGENTS

This application is a continuation of application Ser. No. 07/687,211, filed Apr. 18, 1991, now abandoned, which is a divisional of Ser. No. 07/263,211, filed Oct. 27, 1988, now abandoned.

This invention relates to a novel polypeptide molecule which can be produced by recombinant DNA technology and can be used for many of the existing applications of human serum albumin.

Human serum albumin (HSA) is the most abundant plasma protein, contributing 60% w/w of the total protein content of the plasma. A molecule of HSA consists of a single non-glycosylated polypeptide chain of 585 amino acids of formula molecular weight 66,500. The amino acid sequence of HSA has been established by protein sequence analysis (Meloun et al, 1975, "Complete amino acid sequence of human serum albumin" FEBS. Letters 58:1, 136–317; Behrens et al, 1975, "Structure of human serum albumin" Fed. Proc. 34, 591) and more recently by genetic analysis (Lawn et al, 1981, Nucleic Acids Research 9, 6102–6114). Although there have been discrepancies between the amino acid sequences as published (some being attributable to polymorphisms), FIG. 1 represents the amino acid sequence currently believed to be most representative of the HSA present within the human population.

Because of its relatively small molecular weight and net negative charge at physiological pH (Peters, 1970, "Serum albumin", Adv. Clin. Chem. 13, 37–111), HSA contributes 85% of the osmotic effect of normal plasma. Thus HSA is the principal regulator of plasma volume. A secondary role of HSA is to bind small molecules produced by catabolic processes (for example fatty acids and bilirubin). Albumin represents the principal means for the transport of these key metabolites, which are poorly soluble at physiological pH. Physical, chemical, immunological and limited proteolytic studies of HSA have shown that the molecule is composed of regions of polypeptide chains which retain their conformation after separation from the parent molecule by enzymatic means. These polypeptide chains retain their binding capabilities thereby facilitating the mapping of binding sites for bilirubin, fatty acids and other small molecules to particular regions of the polypeptide chain (Kragh-Hansen, 1981, "Molecular aspects of ligand binding to serum albumin", A. Soc. Pharm. Expt. Ther. 33, 1, 17–53). Much of the information in this area has been reviewed (Brown and Shockley, 1982, "Serum albumin: structure and characterisation of its ligand binding sites").

The indications for the clinical use of therapeutic concentrates of HSA are related principally to its oncotic action as a plasma volume expander. Concentrates of HSA have been used therapeutically since the 1940's, in particular in cases of shock, burns, adult respiratory distress syndrome, and cardiopulmonary bypass. Albumin has also been used in cases of acute liver failure, following removal of ascitic fluid from patients with cirrhosis, after surgery, in acute nephrosis, in renal dialysis, and as a transport protein for removing toxic substances, such as in severe jaundice in haemolytic disease of the new born.

In addition to its use as a therapeutic agent, HSA is a major component of serum added to media used to support the growth of mammalian cells in tissue culture. The consumption of serum and hence of albumin has been greatly increased over recent years as biotechnology and pharmaceutical companies have expanded their tissue culture for research and for production. There is a universal need for lower cost and better regulation of sera for these purposes.

It is known to manipulate the HSA-encoding DNA sequence to express a recombinant polypeptide in microorganisms. Indeed such a recombinant HSA polypeptide has been produced in bacterial species such as *Escherichia coli* (G.B. Patent No. 2 147 903B) and *Bacillus subtilis* (European Patent Application No. 86304656.1) and the yeast *Saccharomyces cerevisiae* (European Patent Publication No. 201 239, Delta Biotechnology Ltd.); thus it is generally accepted that a recombinant polypeptide essentially identical to natural HSA can be produced in a variety of microbial hosts by employing known methods. However, in all cases where recombinant HSA has been produced, the objective has been to produce a molecule which is "nature-identical" to HSA in structure and biological function.

It has now been found that it is advantageous to produce shorter forms of HSA.

One aspect of the present invention provides a polypeptide comprising the N-terminal portion of human serum albumin up to amino acid residue n, where n is 369 to 419, and variants thereof.

The novel polypeptides of the invention are hereinafter referred to as "HSA(1−n)".

The term "human serum albumin" is intended to include (but not necessarily to be restricted to) known or yet-to-be-discovered polymorphic forms of HSA. For example, albumin Naskapi has Lys-372 in place of Glu-372 and pro-albumin Christchurch has an altered pro-sequence. The term "variants" is intended to include (but not necessarily to be restricted to) minor artificial variations in residues 1 to n (such as molecules lacking one or a few residues, having conservative substitutions or minor insertions of residues, or having minor variations of amino acid structure). Thus polypeptides which have 80%, preferably 85%, 90%, 95% or 99%, homology with any HSA (1−n) compound are deemed to be "variants". Such variants are preferably 360 to 430 amino acids long, more preferably 369 to 419 amino acids long. It is also preferred for such variants to be physiologically equivalent to HSA (1−n) compounds; that is to say, variants preferably share at least one pharmacological utility with HSA (1−n) compounds. Furthermore, any putative variant which is to be used pharmacologically should be non-immunogenic in the animal (especially human) being treated.

Conservative substitutions are those where one or more amino acids are substituted others having similar properties such that one skilled in the art of polypeptide chemistry would expect at least the secondary structure, and preferably the tertiary structure, of the polypeptide to be substantially unchanged. For example, typical such substitutions include alanine or valine for glycine, arginine or asparagine for glutamine, serine for threonine and histidine for lysine. Variants may alternatively, or as well, lack up to ten (preferably only one or two) amino acid residues in comparison with any given HSA (1−n); preferably any such omissions occur in the 100 to 369 portion of the molecule (relative to mature HSA itself). Similarly, up to ten, but preferably only one or two, amino acids may be added, again in the 100 to 369 portion for preference. The term "physiologically functional equivalents" also encompasses larger molecules comprising the said 1 to n sequence plus a further sequence at the N-terminal (for example, pro-HSA(1−n), pre-pro-HSA(1−n), met-HSA(1−n), and HSA(1−n) having a suitable leader sequence which is not necessarily native to HSA.

If the HSA (1−n) is to be prepared by culturing a transformed yeast (*S. cerevisiae*) as is described in more detail below, the leader sequence may, for example, be that found naturally with the yeast alpha-factor protein. C-terminal fusion products with other polypeptides of interest may be produced. Known forms and fragments of HSA are clearly to be regarded as excluded from the above definition, for example HSA(1-187), which was a peptic fragment produced in low yield (Geisow and Beaven, Biochem. J. 161, 619-624, 1977 and ibid. 163, 477-484, 1977. These prior articles identify the fragment as 1-386, but it has since become apparent (see, for example, Lawn et al, op-cit.) that this is due to the authors' use of incorrect published sequence information and that the fragment was in fact 1-387). Similarly, a C-terminal fusion protein comprising HSA (1−n) and the remaining HSA residues (numbers n+1 to 585) is not claimed as part of the invention.

Particularly preferred novel HSA(1−n) compounds include HSA(1-373)(i.e. C-terminal Val), HSA(1-388) (i.e. C-terminal Ile), HSA(1-389)(i.e. C-terminal Lys), HSA(1-390)(i.e. C-terminal Gln) and HSA(1-407)(i.e. C-terminal Leu).

The HSA(1−n) molecules are preferably produced by means of recombinant DNA technology (optionally followed by proteolytic digestion), rather than by chemical or enzymatic degradation of natural HSA, or by peptide synthesis. In the case of enzymatic degradation, for example, a trypsin-like enzyme will cleave HSA between Lys(389) and Gln(390) but also concomitantly at other cleavage sites. In the future, peptide synthesis may become more feasible for molecules as long as 419 amino acids, but at present is not a practical proposition. Expression in yeast is particularly preferred.

It has been found that, at least in some situations where the HSA(1−n) compound is produced by culturing a transformed host, some HSA(1−n) compounds which are longer than HSA(1-387) are proteolytically digested back to HSA (1-387) by the enzymes which are naturally present in the system. Thus, one can, if desired, use a nucleotide sequence corresponding to a given HSA(1−n) compound in order to prepare another HSA(1−n) compound.

The new molecules herein described can be used as an effective substitute for either natural HSA or nature-identical recombinant HSA as a plasma volume expander. An advantage of HSA(1−n) over natural HSA and recombinant nature-identical HSA relates to the efficacy of raising the colloid osmotic pressure of blood. The smaller molecular weight (approximately 44 kilodaltons) of the protein of the present invention means that an individual protein dose of only one-half to two-thirds that of natural-HSA or natural-identical recombinant HSA will be required for the equivalent colloid osmotic effect. Consequently, any process for the production of this novel polypeptide by means of recombinant DNA technology may afford significant economic advantages over known processes for the production of nature-identical recombinant HSA, since substantially less proteinaceous material is required to be produced for an effective dose.

Thus, a second aspect of the invention provides a pharmaceutical composition comprising HSA(1−n)plus, where HSA(1−n)plus is HSA(1−n) as defined above or any HSA(1−n) molecules which are known per se but have not been proposed for pharmaceutical use.

HSA (1-387) which, as discussed above, was a fragment produced by chance in a prior art peptic digest of HSA, is particularly preferred as the HSA(1−n)plus in such a pharmaceutical composition. The composition may comprise "variants" of HSA (1-387) as defined above.

A third aspect provides a method of treating a human for shock, burns or other conditions in which albumin is indicated, comprising administering intravenously a blood-bulking or blood-clearing effective non-toxic amount of a sterile non-pyrogenic solution of a polypeptide comprising HSA(1−n)plus.

Further aspects of the invention include (a) vectors, plasmids and transformed microorganisms, including cell lines, encoding HSA(1−n)plus expression; (b) processes for the production of HSA(1−n)plus comprising the fermentation under suitable conditions of a microorganism (including a cell line) so transformed as to express HSA(1−n)plus; and (c) laboratory media comprising HSA(1−n)plus.

A further advantage of at least some HSA(1−n) plus molecules over nature-identical recombinant HSA is that their smaller size and thus reduced amino acid content has been found to lead to an increase in the yield obtained (molecules per cell dry weight) in microbial hosts relative to that obtained currently for nature-identical recombinant HSA. Thus, not only has it been found that the scale of the process can be reduced, but also productivity in the recombinant host organism can be enhanced.

The compounds of the invention may be used as blood-bulking (plasma-expanding) agents in analogous ways and in analogous formulations as HSA itself except that the dose of the HSA(1−n)plus compound (in terms of weight) will generally be less than that of HSA as the oncotic effect of the former is greater. The pharmacist or clinician skilled in the art will readily be able to determine by routine and non-inventive experimentation the optimum dose of the HSA(1−n)plus compound. Generally, the amount of HSA(1−n)plus which is administered will be about two-thirds of the amount of HSA which would be administered.

HSA (1−n) plus compounds may also be used as: (1) substitutes for HSA or, more commonly, bovine serum albumin (BSA) in tissue culture media, thereby reducing the risk of contamination of the medium with, for example, viruses and mycoplasmas; (2) substitutes for BSA in the stationary phase in liquid chromatography for resolution of enantiomers and so on.

EXAMPLES

The invention will now be illustrated by way of example and with reference to the drawings, in which:

FIG. 1 depicts the amino acid sequence currently thought to be the most representative of natural HSA, with (boxed) the alternative C-termini of HSA(1−n);

FIG. 2 depicts the DNA sequence coding for mature HSA;

Figure 7:
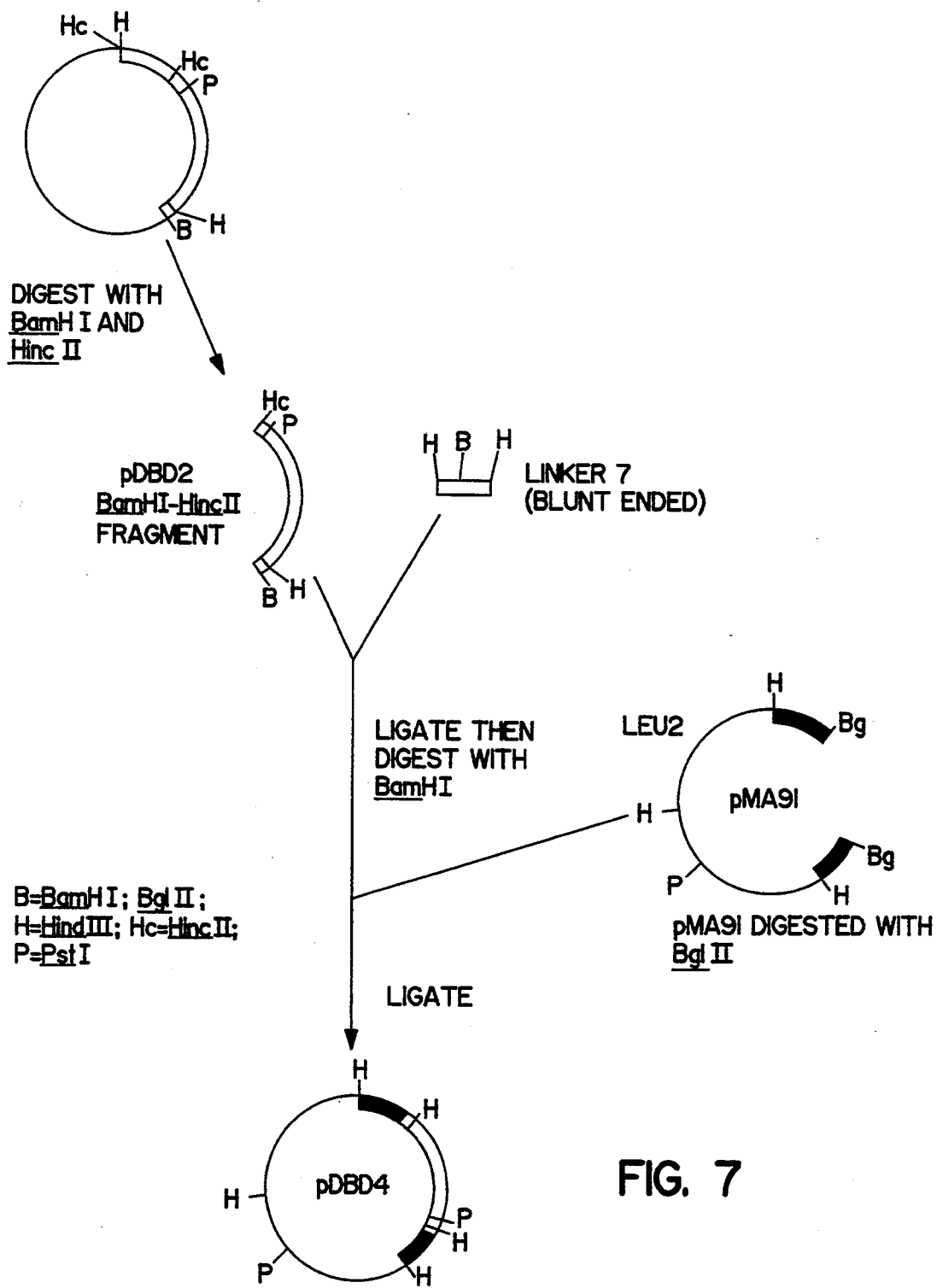

FIG. 7 likewise depicts the construction of pDBD4 from pDBD2 and pMA91.

Figure 8:
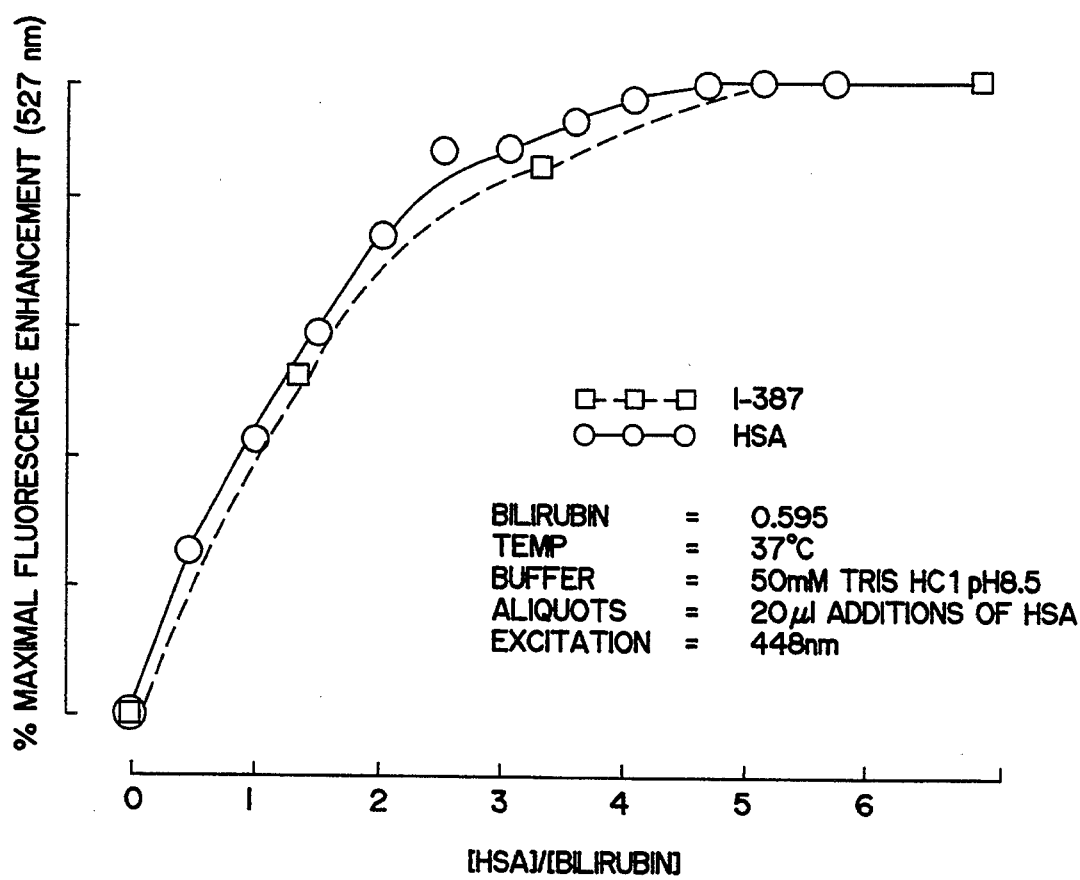

FIG. 8 compares the binding of bilirubin to HSA (1-387) (delta 21) and to clinical grade HSA.

Figure 9:
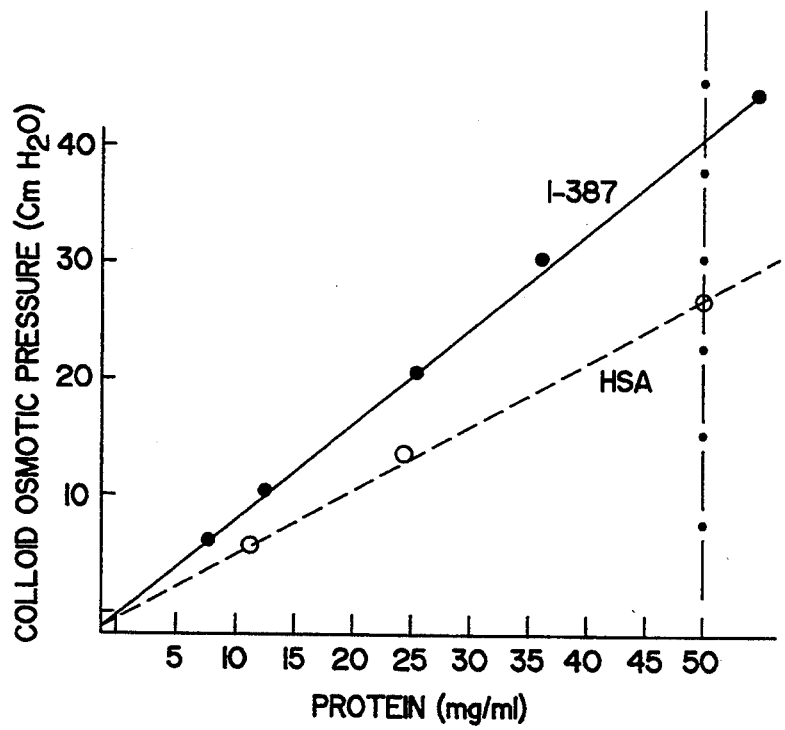

FIG. 9 shows that HSA (1-387)(delta 21) yields a colloid osmotic pressure about one-third higher than that of full-length HSA at a given protein concentration.

Standard recombinant DNA procedures are as described by Maniatis et al (1982) unless otherwise stated. Construction and analysis of M13 recombinant clones was as described by Messing (1983) and Sanger et al. (1977).

The human serum albumin coding sequence used in the construction of the following molecules is derived from the plasmid M13mp19.7 (European Patent Application No. 201 239, Delta Biotechnology Ltd.) or by synthesis of oligonucleotides equivalent to parts of this sequence. Oligonucleotides were synthesised using phosphoramidite chemistry on a Applied Biosystems 380B oligonucleotide synthesizer according to the manufacturer's recommendations (AB Inc., Warrington, Cheshire, England).

EXAMPLE 1: HSA (1-389)

An expression vector was constructed in which DNA encoding the HSA secretion signal and mature HSA up to and including the 389th amino acid, lysine, was placed downstream of the *S. cerevisiae* phosphoglycerate kinase gene (PGK) promoter and followed by a stop codon and the PGK terminator of transcription. This vector was then introduced into *S. cerevisiae* by transformation and directed the expression and secretion from the cells of a molecule representing the N-terminal 389 amino acids of HSA.

Figure 3:
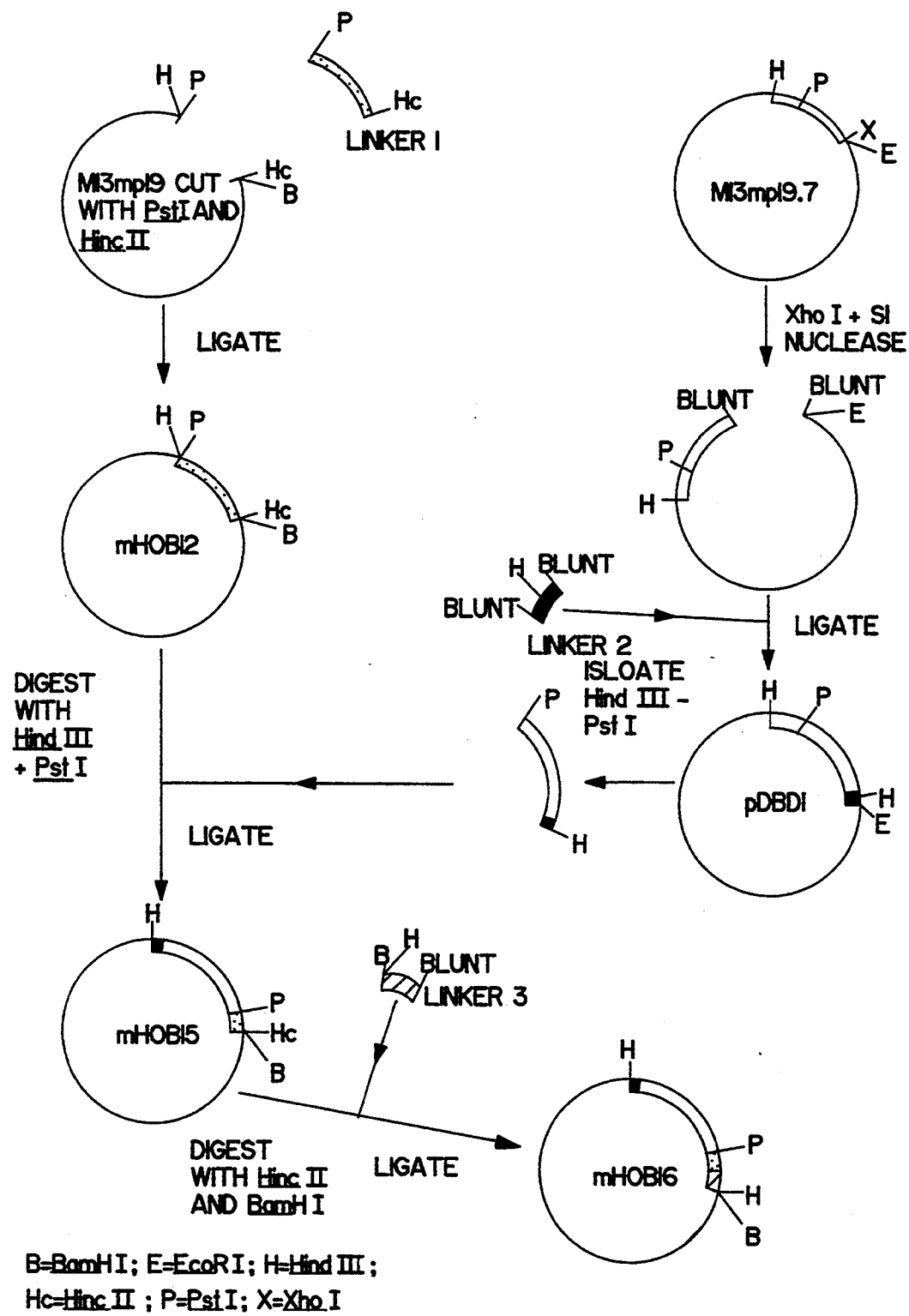
FIG. 3 illustrates, diagrammatically, the construction of mHOB16.

An oligonucleotide was synthesised (Linker 1) which represented a part of the known HSA coding sequence (FIG. 2) from the PstI site (1092, FIG. 2) to the codon for valine 381 wherein that codon was changed from GTG to GTC:

identified by their failure to evolve a blue color on medium containing the chromogenic indicator X-gal (5-bromo-4-chloro-3-indolyl-β-D-galactoside) in the presence of IPTG (isopropylthio-β-galactoside). DNA sequence analysis of template DNA prepared from bacteriophage particles of recombinant clones identified a molecule with the required DNA sequence, designated mHOB12 (FIG. 3).

M13mp19.7 consists of the coding region of mature HSA in M13mp19 (Norrander et al, 1983) such that the codon for the first amino acid of HSA, GAT, overlaps a unique XhoI site thus:

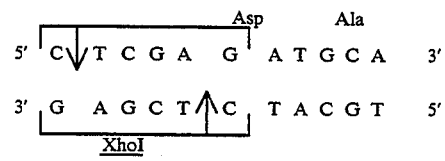

(EPA No. 210239 A1). M13mp19.7 was digested with XhoI, made flush-ended by S1-nuclease treatment and was then ligated with the following oligonucleotide (Linker 2):

Linker 2

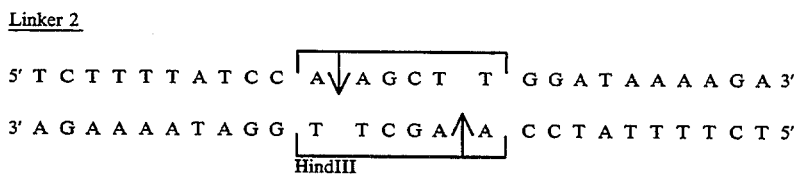

The ligation mix was then used to transfect *E. coli* XL1-Blue and template DNA was prepared from several plaques and then analysed by DNA sequencing to identify a clone, pDBD1 (FIG. 4), with the correct sequence.

Figure 4:
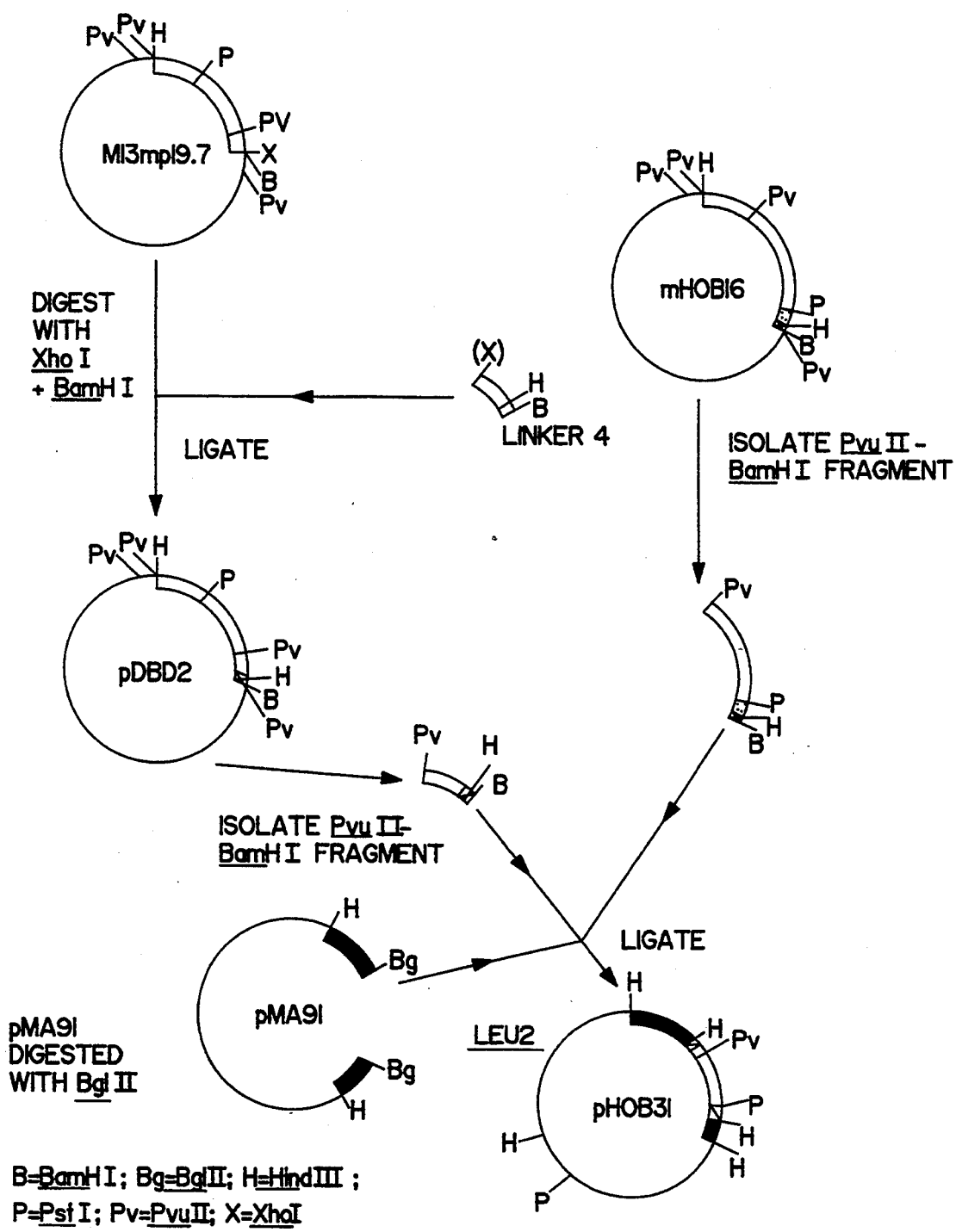
FIG. 4 illustrates, diagrammatically, the construction of pHOB31.

A 1.1 kb HindIII to PstI fragment representing the 5' end of the HSA coding region and one half of the inserted oligonucleotide linker was isolated from pDBD1 by agarose gel electrophoresis. This fragment was then ligated with double stranded mHOB12 previously digested with HindIII and PstI and the ligation mix was then used to transfect *E. coli* XL1-Blue. Single stranded template DNA was prepared from mature bacteriophage particles of several plaques. The DNA was made double stranded in vitro by extension from annealed sequencing primer with the Klenow fragment of DNA polymerase I in the presence of deoxynucleoside triphosphates. Restriction enzyme analysis of this DNA permitted the identification of a clone with the correct configuration, mHOB15 (FIG. 4).

The following oligonucleotide (Linker 3) represents

Linker 1
```
         D   P   H   E   C   Y   A   K   V   F   D   E
5'       GAT CCT CAT GAA TGC TAT GCC AAA GTG TTC GAT GAA
3' ACGT  CTA GGA GTA CTT ACG ATA CGG TTT CAC AAG CTA CTT
         1100                                1120

F   K   P   L   V
    TTT AAA CCT CTT GTC 3'
    AAA TTT GGA GAA CAG 5'
```

Linker 1 was ligated into the vector M13mp19 (Norrander et al, 1983) which had been digested with PstI and HincII and the ligation mixture was used to transfect *E. coli* strain XL1-Blue (Stratagene Cloning Systems, San Diego, Calif.). Recombinant clones were from the codon for the 382nd amino acid of mature HSA (glutamate, GAA) to the codon for lysine 389 which is followed by a stop codon (TAA) and a HindIII site and then a BamHI cohesive end:

Linker 3

```
        E   E   P   Q   N   L   I   K   J
5' GAA GAG CCT CAG AAT TTA ATC AAA TAA GCTTG         3'
3' CTT CTC GGA GTC TTA AAT TAG TTT ATT CGAACCTAG 5'
```

This was ligated into double stranded mHOB15, previously digested with HincII and BamHI. After ligation, the DNA was digested with HincII to destroy all non-recombinant molecules and then used to transfect E. coli XL1-Blue. Single stranded DNA was prepared from bacteriophage particles of a number of clones and subjected to DNA sequence analysis. One clone having the correct DNA sequence was designated mHOB16 (FIG. 4).

A molecule in which the mature HSA coding region was fused to the HSA secretion signal was created by insertion of Linker 4:

Linker 4

```
        M   K   W   V   S   F   I   S   L   L   F   L
5' GATCC ATG AAG TGG GTA AGC TTT ATT TCC CTT CTT TTT CTC
       G TAC TCC ACC CAT TCG AAA TAA AGG GAA GAA AAA GAG

Figure 5:
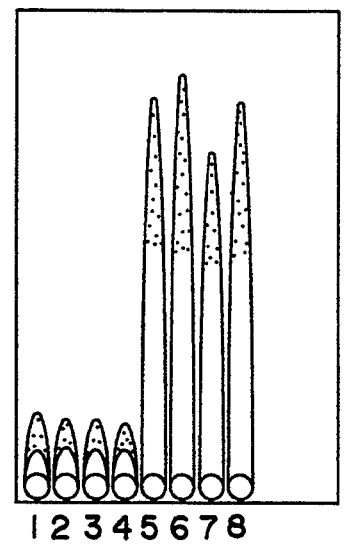
FIG. 5 is a copy of a rocket electrophoretogram showing the increased yield of HSA(1-389) over complete HSA.

F   S   S   A   Y   S   R   G   V   F   R   R
   TTT AGC TCG GCT TAT TCC AGG GGT GTG TTT CG       3'
   AAA ACG AGC CGA ATA AGG TCC CCA CAC AAA GCAGCT 5'
``` into BamHI and XhoI digested M13mp19.7 to form pDBD2 (FIG. 5). In this linker the codon for the fourth amino acid after the initial methionine, ACC for threonine in the HSA pre-pro leader sequence (Lawn et al, 1981), has been changed to AGC for serine to create a HindIII site.

The 5' end of this construction was removed as a BamHI to PvuII fragment and ligated with the PvuII to BamHI fragment of double stranded mHOB16 (representing the 3' end of the truncated HSA gene) into pMA91 (Mellor et al, 1983) at the BglII site to form pHOB31 (FIG. 4). This molecule contains the truncated HSA coding region with the HSA secretion signal between the S. cerevisiae PGK gene promoter and terminator such that the 5' end of the gene abuts the promoter. The molecule also contains a selectable marker for yeast transformation, LEU2, and part of the yeast 2um plasmid to permit autonomous replication in yeast.

The plasmid pHOB31 was introduced into S. cerevisiae AH22 (Hinnen et al, 1978) by transformation using standard procedures (Beggs, 1978). Purified transformants were grown in YEPD broth (1% yeast extract, 2% peptone, 2% glucose) for 3 days at 30° C. and the culture supernatant was then analysed, successfully, for the presence of HSA-related material by rocket gel electrophoresis. FIG. 5 shows the electrophoretogram: the yield of HSA-related material from transformants harboring a plasmid encoding HSA(1-389) is demonstrably higher than the yield from a transformant secreting mature, natural, HSA.

However, production of HSA (1-389) gave a product indistinguishable from HSA (1-387)(see Example 2) by both amino-terminal and carboxy-terminal sequence analysis. This is probably explained by the efficient removal of the COOH-terminal sequence Ile-Lys.

EXAMPLE 2: HSA (1-387)

The construction of a plasmid encoding HSA (1-387) was identical to the procedure for construction of the HSA (1-389) plasmid, pHOB31, except that the linker 3 was substituted by linker 5 (shown below) which represents the region from the codon for the 382nd amino acid of mature HSA (glutamate, GAA) to the codon for leucine 387 which is followed by a stop codon and a HindIII site and then a BamHI cohesive end:

Linker 5

```
        E   E   P   Q   N   L   Stop
5' GAA GAG CCT CAG AAT TTA TAA GCTTG       3'
3' CTT CTC GGA GTC TTA AAT ATT CGAACCTAG 5'
```

The remainder of the construction was as detailed above for pHOB31 and resulted in the plasmid pDBD5.

EXAMPLE 3: (1-369)

In order to construct a plasmid encoding HSA (1-369), a linker was synthesised representing the region from the PstI site of mature HSA (position 1092, FIG. 3) to the codon for cystine 369 which was followed by a stop codon (TAA), a HindIII site and then a BamHI cohesive end:

Linker 6

```
           D   P   H   E   C   Stop
5'        GAT CCT CAT GAA TGC TAA GCTTG
3' A CGT CTA GGA GTA CTT ACG ATT CGAACCTAG
```

Figure 6:
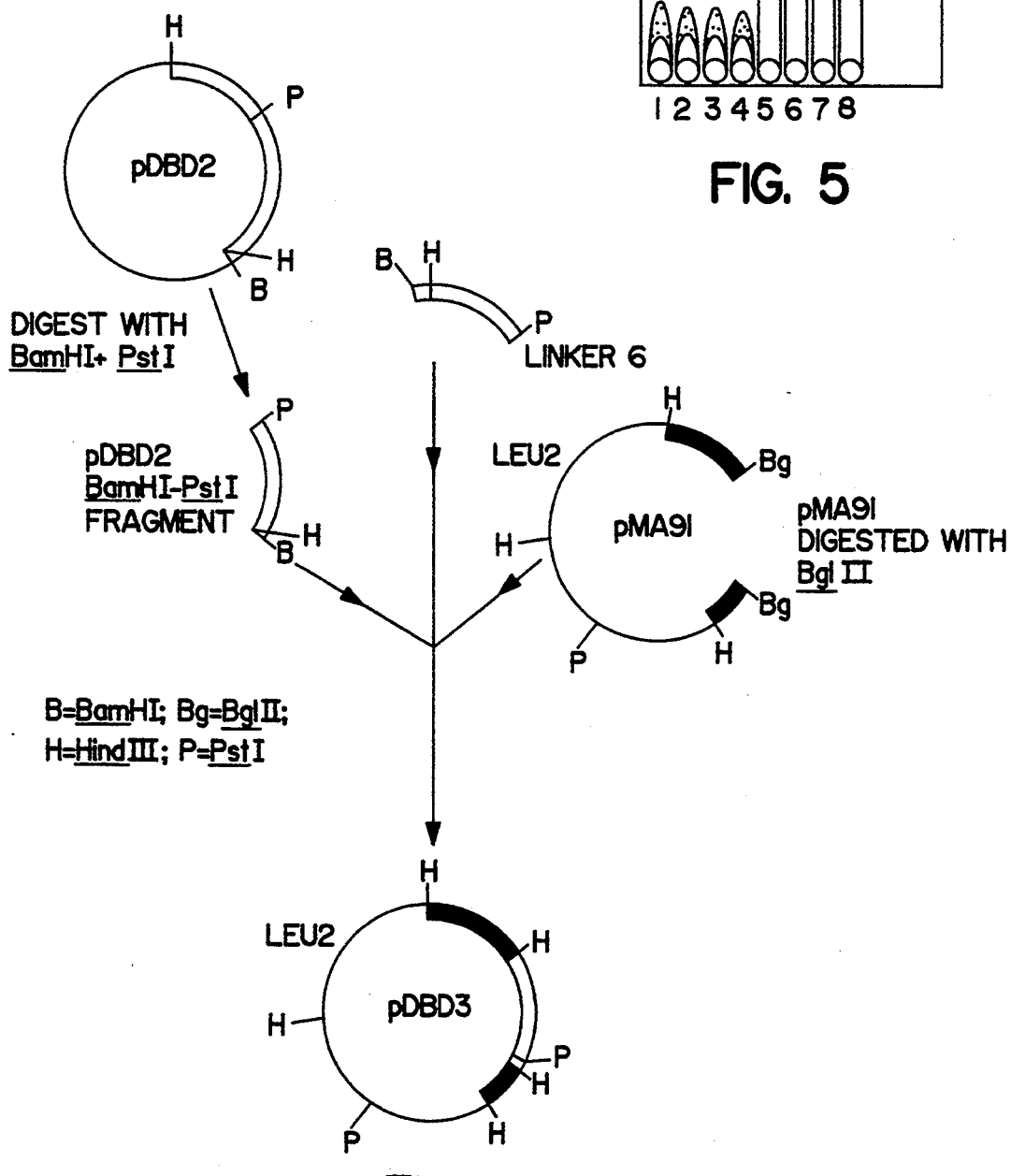
FIG. 6 illustrates the construction of pDBD3 from pDBD2 and pMA91.

This linker was ligated with the BamHI PstI fragment of pDBD2, representing the 5' part of preproHSA, into pMA91 at the BglII site. A plasmid with the correct configuration was termed pDBD3 (FIG. 6).

Production of HSA (1-369) by culturing S. cerevisiae transformed with pDBD3 gave low yields, indicating that the product may have been unstable in the yeast expression system used.

EXAMPLE 4: HSA (1-419)

For the construction of a plasmid encoding HSA (1-419) the BamHI-HincII fragment of pDBD2 was ligated with an annealed self-complementary oligonucleotide (linker 7):

Linker 7

5' ATAAGCTTGGATCCAAGCTTAT 3' and then the ligation mix was digested with BamHI and the fragment was ligated into pMA91 to give pDBD4 (FIG. 7). In this construct the HincII site (1256, FIG. 3) of pDBD2 creates a blunt end after the second base of the codon for serine 419 and this codon is reformed by the linker 6 such that this codon is followed by a stop codon, a HindIII site and a BamHI site.

Expression of HSA (1–419) via plasmid pDBD5 in *S. cerevisiae* produced a molecule with the correct amino terminal sequence (Asp-Ala-His . . . ) but leucine and not serine was the COOH-terminal residue. Attempts to isolate the COOH-terminal peptide using a covalent label which should attach to cysteine 392 also were unsuccessful. It was concluded that proteolysis of part of the COOH-terminus of HSA (1–419) occurred. This is consistent with the observation of a small percentage of proteolysis in the same position of full-length HSA produced in an analogous manner in yeast. (Sleep et al, 1988).

EXAMPLE 5: Fermentation of HSA(1−n)plus-producing Yeast

A laboratory fermenter is filled to half its normal working volume with an initial "batch" medium containing 50 ml/l of a salts mixture (containing 114 g/l $KH_2PO_4$, 12 g/l $MgSO_4$, 3.0 g/l $CaCl_2.6H_2O$, 2.0 g/l $Na_2$ EDTA; 10 ml/l of a trace elements solution containing 3 g/l $ZnSO_4.7H_2O$, 10 g/l $FeSO_4.7H_2O$, 3.2 g/l $MnSO_4.4H_2O$, 79 mg/l $CuSO_4.5H_2O$, 1.5 g/l $H_3BO_3$, 0.2 g/l KI, 0.5 g/l $Na_2MoO_4.2H_2O$, 0.56 g/l $CoCl_2.6H_2O$, 75 ml/l $H_3PO_4$; 20 g/l sucrose; 50 ml/l of a vitamins mixture containing 1.6 g/l Ca pantothenate, 1.2 g/l nicotinic acid, 12.8 g/l m inositol, 0.32 g/l thiamine HCl and 8 mg/l pyridoxine HCl and 8 mg/l biotin. An equal volume of "feed" medium containing 100 ml/l of the salts mixture, 20 ml/l of trace elements solution 500 g/l sucrose and 100 ml/l vitamin solution is held in a separate reservoir connected to the fermenter by a metering pump.

The fermenter is inoculated with *Saccharomyces cerevisiae* which has been transformed as above with plasmid pDBD3 from Example 2. The pH is maintained at 5.7±0.2 by automatic addition of ammonia or sulphuric acid, the temperature is kept at 30° C. and the stirred speed is adjusted to give a dissolved oxygen tension (DOT) of >20% air saturation at 1 v/v/min air flow rate. When the initial substrate has been consumed, the metering pump is turned on, maintaining a growth rate of approximately 0.15 $h^{-1}$. The pump rate is increased to maintain this growth rate until the stirrer speed reached its maximum value at which point it is not possible to increase the pump rate any further without causing the DOT to fall below 15% air saturation which is the minimum value permitted to occur. PPG 2000 is added in response to a foam sensor. None is added until over 50% of the feed solution had been added. The final level of addition is 0.2 g/l.

HSA(1–387) is secreted into the medium.

EXAMPLE 6: Binding of Bilirubin to HSA(1–387)

Binding of the heme metabolite, bilirubin, to HSA (1–387) was carried out by a fluorescence enhancement method (Beaven and Gratzen (1973) Eur. J. Biochem. 33, 500–510). FIG. 8 shows that the enhancement of bilirubin fluorescence as a function of protein/bilirubin ratio is indistinguishable for HSA(1–387) and clinical grade HSA.

The interaction of HSA and bilirubin is very sensitive to the conformation of the protein (Beaven and Gratzen, loc. cit.) and these results indicate that no gross alteration in conformation of the region of HSA represented by HSA(1–387) has occurred through the expression of a shorter molecule.

EXAMPLE 7: Oncotic Behaviour of HSA(1–387)

HSA(1–387) was concentrated in 0.9% w/v saline to a final protein concentration of 54 mg/ml. Dilutions of this concentrate, together with dilutions of a clinical grade HSA (100 mg/ml), were compared for osmotic effect in a colloid osmometer. FIG. 9 indicates that HSA(1–387) gives a colloid osmotic pressure approximately one-third higher than that of full-length HSA at a given protein concentration. Importantly, the increase in colloid osmotic pressure with protein concentration is approximately linear over a range up to 5% w/v, which represents the concentration in plasma.

This indicates that HSA(1–387) does not self-associate appreciably within a useful working clinical concentration range.

EXAMPLE 8: Formulations for Injection

The HSA(1−n)plus of the invention may be presented in container sizes ranging from 20 ml to 500 ml, with the concentration thereof varying (typically) from 2% to 17% for example 3%, 13% or 17%.

The solution for administration is sterile and pyrogen free. A 3% solution is osmotically similar to human plasma. At least 96% of the total protein is preferably albumin. The sodium ion content is generally between 130–160 mmol/liter and the potassium ion content is generally not more than 2 mmol/liter. The pH is adjusted to 6.9±0.5. The concentration of citrate is generally no more than 20 mmol/liter and may be absent altogether.

Stabilizers may be used, for example either 0.16 millimole sodium acetyl tryptophanate, or 0.08 millimole sodium acetyl tryptophanate and 0.08 millimole sodium caprylate per gram of HSA(1−n)plus.

REFERENCES

Beggs, J. D. (1978), Nature, 275, 104–109.

Brown, J. R. and Shockley, P., (1982) in "Lipid-Protein Interactions" 1, 25–68, Eds. Hayes, O. and Jost, P. C.

Hinnen, A. et al (1978), Proc. Natl. Acad. Sci. U.S.A., 75, 1929–1933.

Lawn, R. M. et al (1981), Nucl. Acid. Res. 9, 6103–6114.

Maniatis, T. et al (1982), Molecular cloning: A laboratory manual. Cold Spring Harbor Laboratory, Cold Spring Harbor, New York.

Mellor, J. et al (1983), Gene, 24, 1–14.

Messing, J. et al (1983), Methods Enzymol. 101, 20–78.

Norrander, J. et al (1983), Gene, 26, 101–106.

Sanger, F. et al (1977), Proc. Natl. Acad. Sci. U.S.A., 74, 5463–5467.

Sleep, D. Belfield, G. P. and Goodey, A. R. (1988) Yeast 4, S168.

We claim:

1. A method of expanding the plasma volume of the blood of a mammal, comprising administering intravenously to said mammal an effective amount of a polypeptide which is an N-terminal fragment of mature human serum albumin (HSA) consisting of residues 1 through n, where n is from 369 to 419, or an oncotically active variant of said fragment, wherein said variant is a polypeptide of at least 360 and not more than 430 amino acids, exhibits at least 80% sequence identity with the corresponding HSA N-terminal fragment, and which differs from said fragment only by conservative substitutions.

2. A method according to claim 1, wherein the polypeptide is selected from the group consisting of HSA(1-373), HSA(1-388), HSA(1-389), HSA(1-390), HSA(1-407), and a variant of one of the foregoing HSA fragments, said variant exhibiting at least 80% sequence identity with the corresponding HSA N-terminal fragment and differing therefrom only by conservative substitutions.

3. A method according to claim 1 wherein the administered polypeptide is HSA(1-387).

* * * * *